(12) United States Patent
Doleman et al.

(10) Patent No.: US 6,844,197 B1
(45) Date of Patent: Jan. 18, 2005

(54) METHOD FOR VALIDATING THAT THE DETECTION ABILITY OF A SENSOR ARRAY MIMICS A HUMAN NOSE DETECTION ABILITY

(75) Inventors: Brett J. Doleman, Pasadena, CA (US); Nathan S. Lewis, La Canada, CA (US); Erik J. Severin, San Marino, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/293,669

(22) Filed: Apr. 16, 1999

Related U.S. Application Data

(60) Provisional application No. 60/082,095, filed on Apr. 17, 1998.

(51) Int. Cl.[7] ............................................. G01N 27/416
(52) U.S. Cl. .............................. 436/151; 436/8; 436/9; 436/149; 436/150; 422/82.01; 422/82.02; 422/83; 422/98
(58) Field of Search ............................ 422/68.1, 82.01, 422/82.02, 82.05, 82.06, 83, 84, 98; 436/149, 150, 151, 164, 8, 9, 11, 12–15; 73/23.34, 23.36

(56) References Cited

U.S. PATENT DOCUMENTS

| | | | | |
|---|---|---|---|---|
| 5,145,645 A | * | 9/1992 | Zakin et al. .................... | 422/98 |
| 5,231,030 A | * | 7/1993 | Deetz et al. .................... | 436/8 |
| 5,234,835 A | * | 8/1993 | Nestor et al. ................... | 436/11 |
| 5,246,859 A | * | 9/1993 | Nelson et al. .................. | 436/11 |
| 5,499,023 A | * | 3/1996 | Goldschmidt .......... | 340/870.37 |
| 5,623,095 A | * | 4/1997 | Beller ........................ | 73/61.49 |
| 5,629,872 A | * | 5/1997 | Gross et al. ................. | 364/554 |
| 5,653,939 A | * | 8/1997 | Hollis et al. ................... | 422/50 |
| 5,683,569 A | * | 11/1997 | Chung et al. ................ | 205/775 |
| 5,761,090 A | * | 6/1998 | Gross et al. ............ | 364/551.01 |
| 5,763,760 A | * | 6/1998 | Gumbrecht et al. .......... | 73/1.06 |
| 5,832,411 A | * | 11/1998 | Schatzmann et al. ......... | 702/23 |
| 5,928,609 A | * | 7/1999 | Gibson et al. ................. | 422/90 |
| 5,951,846 A | * | 9/1999 | Lewis et al. ................. | 205/787 |
| 5,959,191 A | * | 9/1999 | Lewis et al. ................ | 73/31.05 |
| 6,066,249 A | * | 5/2000 | Manzoni et al. ............. | 205/782 |
| 6,101,406 A | * | 8/2000 | Hacker et al. .............. | 600/322 |
| 6,356,857 B1 | * | 3/2002 | Qin et al. .................... | 702/185 |

OTHER PUBLICATIONS

Gardner et al., "A brief history of electronic noses," *Sensors and Actuators B*, 18–19:211–220 (1994).

Hatfield et al., "Towards an integrated electronic nose using conducting," *Sensors and Actuators B*, 18–19:221–228 (1994).

J. Travis, "Scientists begin to decipher the alphabet of odors," *Science News*, 155:236–238 (1999).

Krautwurst et al., "Identification of Ligands for Olfactory Receptors by Functional Expression of a Receptor Library," *Cell*, 95:917–926 (1998).

Malnic et al., "Combinatorial Receptor Codes for Odors," *Cell*, 96:713–723 (1999).

* cited by examiner

*Primary Examiner*—Maureen M. Wallenhorst
*Assistant Examiner*—Dwayne K Handy
(74) *Attorney, Agent, or Firm*—Foley & Lardner LLP

(57) ABSTRACT

The present invention relates to methods for matching and validating the response intensity of a sensor array to an odorant with the detection threshold of a human nose.

11 Claims, 5 Drawing Sheets

METHOD FOR VALIDATING THAT THE DETECTION ABILITY OF A SENSOR ARRAY MIMICS A HUMAN NOSE DETECTION ABILITY

CROSS-REFERENCES TO RELATED APPLICATIONS

This application claims priority to U.S. Provisional Patent Application Ser. No. 60/082,095, filed Apr. 17, 1998, the disclosure of which is incorporated herein by reference in its entirety for all purposes.

BACKGROUND OF THE INVENTION

Perception of odor is a physical mechanism by which information is processed in the brain. Humans are able to detect an unlimited number of dissimilar odors and in dilutions of up to one part in $10^9$. It is believed that the brain is able to evaluate and identify tens or possibly hundreds of thousands of different odors. The brain is able to recognize these odors and associate them with likes, dislikes, events and experiences. According to the chemical theory of olfaction, molecules of odors, or odorants, are conveyed to the olfactory epithelium by convection, diffusion or both and directly or indirectly induce changes in the olfactory receptors.

It is believed that the human nose detects smells when odorants strike a region on the olfactory neurons, the cells that contain the odorant receptors. Axons extend from these cells to the olfactory bulb, which is the brain region that processes olfactory information. Recently, it has been found that individual odorants activate multiple receptors. Moreover, individual receptors respond to multiple odorant (see, B. Malnic et al., Cell, (1999) Vol 96, 713–723). As described in the foregoing article, the researchers concluded that the combination of receptors that the activated by an odorant determines the smell that humans perceive. It is believed that odorants activate a combination of olfactory neurons giving rise to a combinatorial code, which encodes odorant identities.

Moreover, it is known that a slight change in an odorant's structure can have a dramatic affect on how the odorant is perceived. Octanol has a sweet, orange, rosy, fresh and waxy smell, whereas octanoic acid has a rancid, sour, repulsive and sweaty smell. Although these odorants differ only by the oxidation state of one carbon atom, they have markedly different perceived smells. In this instance, the foregoing study concluded that the odorants triggered overlapping, yet distinct odorant receptors.

The human nose measures odors by their intensity. The threshold value of one odor to another can vary greatly. The detection threshold is the minimum intensity necessary for detection without necessarily identifying the odor. In human olfaction, high odor detection thresholds are observed for odorants that are gases under standard pressure and temperature conditions. Odorants with low vapor pressures generally have low odor detection thresholds (see, Devos, M. et al., *Standardized Human Olfactory Thresholds*, (Oxford University Press, New York), pp. 165 (1990)).

An electronic nose is an instrument used to detect vapors or chemical analytes in gases, solutions, and solids. In general, an electronic nose is a system having an array of sensors that are used in conjunction with pattern-recognition algorithms. Using the combination of an array of sensors, which produce a fingerprint of the vapor or gas, the recognition algorithms can identify and/or quantify the analyte(s) of interest. The electronic nose is thus capable of recognizing unknown odorants.

During use, an electronic nose is presented with a substance, such as an odor or vapor, and the sensor converts the input of the substance into a response, such as an electrical response. The response is then compared to known responses that have been stored previously. By comparing the unique chemical signature of an unknown substance to "signatures" of known substances, the unknown analyte can be determined. A variety of sensors can be used in electronic noses that respond to various classes of gases and odors.

In an effort to construct better electronic noses, attempts have been made to understand odorant detection thresholds that are displayed by the human olfactory sense. Moreover, in an attempt to correlate trends in odor intensity with specific microscopic and macroscopic properties of various odorants, structure-activity relationships have been formulated. For example, researchers have proposed that trends in detection thresholds arise from the presence of steric and other functional groups in olfactory receptors (see, Ohloff, G., *Scent and Fragrances, the Fashion of Odors and Their Chemical Perspectives*, (Springer-Verlag, New York), pp. 238 (1994); Amoore, J. E., *Molecular Basis of Odour*, (Charles C. Thomas, Springfield, Ill., pp. 200 (1970)). Such receptors can then respond to features such as molecular length and polarity (see, Amoore, J. E., *Molecular Basis of Odour*, (Charles C. Thomas, Springfield, Ill.), pp. 200 (1970); Dravnieks, A. in *Flavor Quality: Objective Measurement*, (American Chemical Society, Washington), pp. 11–28 (1977); Edwards, P. A. et al., *Chemical Senses* 14, 281–291 (1989); Edwards, et al., *Chemical Senses* 16, 447–465 (1991)). Other researchers have empirically correlated odor detection thresholds with macroscopic properties of the odorant such as the boiling point of the odorant molecules (see, Abraham, M. H. in *Indoor Air and Human Health*, (CRC Press, New York), pp. 67–91 (1996); Greenberg, M. J. in *Odor Quality and Chemical Structure*, (American Chemical Society, Washington), pp. 177–194 (198 1); Laffort, P. et al., *N.Y. Acad. Sci.* 237, 192 (1974)). Further, other researchers have noted the correlation between odor thresholds and the vapor pressure of the odorant (Moulton, D. G. et al., *Quart. J. Exp. Psychol.* 12, 99–109 (1960); Cometto-Muñiz, J. E. et al., *Indoor Air* 4, 140–145 (1994); Cometto-Muñiz, J. E. et al., *Physiol. Behav.* 48, 719–725 (1990); Mullens, L. J., *Ann. New York Acad. Sci.* 62, 247–276 (1955); Ottonson, D. *Acta Physio. Scand.* 43, 167–181 (1958)).

In view of the foregoing, what is needed in the art is a method that can match the response intensity of a sensor array to an odorant with the detection threshold of a human nose responding to the same odorant. The present invention fulfills this and other needs.

SUMMARY OF THE INVENTION

Attempts have been made to understand the odorant detection response that is displayed by the human olfactory sense in an effort to construct better electronic noses. Moreover, a method is needed that will match the response intensity of a sensor array with that of the human nose. As such, in one aspect, the present invention provides a method for matching a response intensity of a sensor array to an odorant with the detection threshold of a human nose to the same odorant, the method comprising: exposing the odorant to an array of sensors to produce a response intensity, thereby matching the response intensity of the sensor array to the detection threshold of the human nose.

The inventors have surprisingly discovered that odorants with very different vapor pressures have similar sensor responses if the same fractions of their vapor pressures are measured. Thus, the response intensity of an individual sensor is essentially independent of the odorant, if the odorant is present in the gas phase at a constant fraction of its vapor pressure. It is shown herein that electronic nose sensors produce nearly the same odor response intensity from their raw signal outputs at a constant fraction of the vapor pressure of pentane, as for a constant fraction of the vapor pressure of tetradecane. Thus, it has now been discovered a sensor array will elicit the same response intensity for a first odorant as that of a second odorant if the two odorants are present in the gas phase at a constant fraction of their particular vapor pressure. This principle is the same principle upon which the human nose functions. Thus, the present invention provides a process for matching the intensity of a sensor array responding to an odorant with the detection threshold of a human nose responding to the same odorant.

In a particularly preferred embodiment, the sensor array comprises sorption-based sensors. These sorption-based sensors include, but are not limited to, chemiresistors, such as conducting/nonconducting composites, bulk organic conducting polymer sensors, surface acoustic wave detectors, dye-based optical fibers and metal oxide sensors. Other sorption-based sensors suitable for use in the present invention are well known to the those of skill in the art.

Moreover, in another aspect, the present invention relates to a method for validating that a sensor array response intensity matches a human nose detection threshold, the method comprising:

(a) contacting the sensor array with a constant fraction of a known vapor pressure of a first odorant to produce a first response intensity;

(b) contacting the sensor array with the constant fraction of a known vapor pressure of a second odorant to produce a second response intensity; and (c) comparing the first response intensity to the second response intensity, thereby validating that the sensor array response intensity matches the human nose detection threshold.

In still other aspects, the present invention provides a method of predicting the detection threshold of a human nose to an odorant, the method comprising: exposing the odorant to an array of sensors to produce a response intensity, thereby predicting the detection threshold of the human nose.

These and other features and advantages will be more apparent when read with the accompanied figures and detailed description that follows.

DETAILED DESCRIPTION OF THE INVENTION AND PREFERRED EMBODIMENTS

Figure 1A:
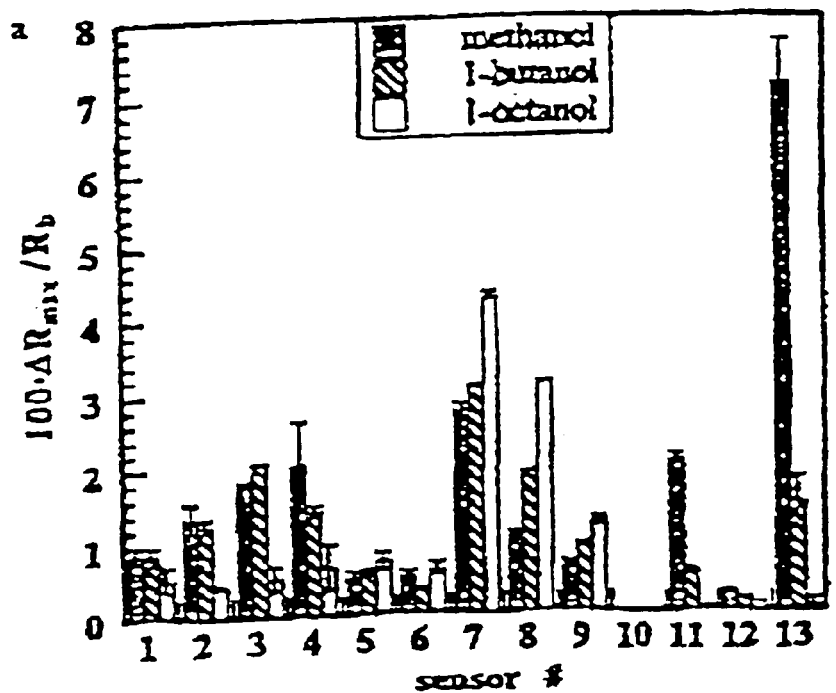
FIGS. 1A-B are histograms showing the response patterns of a 13-sensor array of carbon black-polymer sensors exposed in air. Panel A shows methanol at 11 torr, 1-butanol at 0.57 torr and 1-octanol at $5.8–10^{-3}$ torr. Panel B shows n-pentane at 46 torr, n-nonane at 0.37 torr and n-tetradecane at $8.5–10^{-4}$ torr. The odorant partial pressures correspond to 10% of their vapor pressures in ambient air. Each histogram bar represents the average over 6 exposures of a single sensor to a single odorant for 5 minutes. The error bars represent one standard deviation in each sensor's responses. The polymers in sensors numbers 1–13 were 1) poly(4-vinyl phenol), 2) poly($\alpha$-methyl styrene), 3) poly(vinyl acetate), 4) poly(sulfone), 5) poly(caprolactone), 6) poly(ethylene-co-vinyl acetate) (82% ethylene), 7) poly(ethylene oxide), 8) poly(ethylene), 9) poly(butadiene), 10) poly(vinylidine fluoride), 11) poly(n-butyl methacrylate), 12) poly(epichlorohydrin) and 13) poly(ethylene glycol).

In certain aspects, the present invention relates to a method for matching a response intensity of a sensor array to an odorant with the detection threshold of a human nose to the same odorant, the method comprising: exposing the odorant to an array of sensors to produce the response intensity, thereby matching the response intensity of the sensor array to the detection threshold of the human nose.

Various sensors suitable for detection of odorants include, but are not limited to: surface acoustic wave (SAW) sensors; conductive composites; chemiresistors; conducting polymer sensors; organic semiconducting gas sensor; dye-based optical fibers and Langmuir-Blodgett film sensors. Preferably, the sensors described in U.S. Pat. No. 5,571,401, issued to Lewis et al., are used, the teachings of which is incorporated herein by reference.

Briefly, the sensors described in U.S. Pat. No. 5,571,401 are conducting materials and nonconducting materials arranged in a matrix of conducting and nonconducting regions. The nonconductive material can be a nonconducting polymer such as polystyrene. The conductive material can be a conducting polymer, carbon black, an inorganic conductor and the like. The sensor arrays comprise at least two sensors, typically about 32 sensors and, in certain instances, about 1000 to 10,000 or more sensors. The array of sensors can be formed on an integrated circuit using semiconductor technology methods, an example of which is disclosed in PCT Patent Application WO99/08105, entitled "Techniques and Systems for Analyte Detection," published Feb. 19, 1999, and incorporate herein by reference.

In certain embodiments, the electronic nose of the present invention is an array of sensors, wherein each sensor consists of a dispersion of carbon black particles in a swellable, insulating organic polymer film. Swelling of each carbon black-polymer composite in response to the presence of an odorant produces a response, such as a change in the electrical resistance of the sensor film. In certain aspects, the pattern of responses produced by an array of chemically different carbon black-polymer composites identifies the odorant (analyte), and the pattern height is correlated with the odorant concentration.

In certain preferred embodiments, the sensors are fabricated and their characteristics measured, as described previously (Lonergan, M. C., et al., *Chem Mater.* 8, 2298–2312 (1996)). Briefly, as described therein, individual sensor elements can be prepared by a single dip of a polished cleaved capacitor into 10 mL solutions that contain 80 mg of dissolved nonconducting polymer and 20 mg of carbon black. After removal from the solution, the liquid is shaken off and dried prior to use. Various substrates can be used such as surface mount universal boards (surfboards, part number 6012 from Capital Advanced Technologies Inc.), glass slides or capacitors. During measurements, partial pressures of the odorants are fixed at a constant fraction of their vapor pressures at a particular temperature, such as 22° C. Vapor pressure values can be calculated using accepted formulas described in the literature (Yaws, C. L. et al., *Handbook of Vapor Pressure*, (Gulf Publishing Company, London), pp. 1125 (1994)).

As will be apparent to those of skill in the art, the sensors making up the array of the present invention can be made up of various sensor types as set forth above. For instance, the sensor array can comprise a conducting/nonconducting regions sensor, a SAW sensor, a metal oxide gas sensor, a conducting polymer sensor, a Langmuir-Blodgett film sensor, and combinations thereof In certain embodiments, the resistance change of a sensor is reversible, is linear over at least an order of magnitude of odorant concentration, and is quite reproducible.

As used herein, the phrase "response intensity of a sensor array" refers to the magnitude of the reaction of the sensor array to an odorant stimulus. This reaction or response is preferably an electrical response. Suitable electrical responses include, but are not limited to, resistance, capacitance and inductance. The response intensity can refer to the mean response intensity or mean signal response that is defined as the average of all sensor responses in the electronic nose array to an odorant. In an alternative embodiment, response intensity refers to the largest response of a single sensor or a group of sensors to a particular odorant which give the greatest magnitude of response.

As used herein, the phrase "detection threshold of a human nose" refers to detection of an odorant at the human odor detection threshold. The odor detection threshold is defined, as the concentration at which the presence of an odor can be identified as compared to a moist air blank, but the quality of the odor cannot typically be determined. These values are available from several published sets of psychophysical data, for instance in Devos et al., *Standardized Human Olfactory Thresholds*, (Oxford University Press, New York), pp. 165 (1990)), the teachings of which are incorporated herein by reference. Alternatively, these values can be determined empirically by methods well known to those of skill in the art.

As used herein, the phrase "matching response intensity of a sensor array with the detection threshold of the human nose," refers to the discovery that a comparison between human and electronic nose response data is consistent with a sorption-based effect dominating the odor intensity determinations and, thus, that the electronic nose of the present invention and their response intensities correlate, i.e., match, mimic or track, the mean human olfactory odor detection thresholds, when based on odorant partial pressure. The response intensity increase as the vapor pressure of the odorant increases. In human olfaction, high odor detection thresholds are observed for odorants that are gases under standard pressure and temperature conditions. Odorants with low vapor pressures generally have low odor detection thresholds.

In the methods of the present invention, the odorants include, but are not limited to, alkanes, alkenes, alkynes, dienes, alicyclic hydrocarbons, arenes, alcohols, ethers, ketones, aldehydes, carbonyls, carbanions, heterocycles, polynuclear aromatics, organic derivatives, biomolecules, microorganisms, bacteria, viruses, sugars, nucleic acids, proteins, isoprenes, isoprenoids, fatty acids and their derivatives.

The identification of odorants present in the vapor is facilitated by various analyses suitable for identifying odorants, classifying odorants and quantifying concentration. Suitable analyses include, but are not limited to, principal component analysis, Fischer linear analysis, neural networks, genetic algorithms, fuzzy logic, pattern recognition, and other algorithms. The various algorithms are resident on a computer or computer network. Thus, the electronic noses of the present invention comprise a sensor array connected to a response measuring apparatus; and a computer comprising a resident algorithm, wherein the response measuring apparatus is capable of assembling the responses into a response profile for odorant identification.

The methods of the present invention are applicable to a wide variety of applications. Suitable applications include, but are not limited to, environmental toxicology and remediation, biomedicine, materials quality control, food and agricultural products monitoring, heavy industrial manufacturing, ambient air monitoring, worker protection, emissions control, product quality testing, oil/gas petrochemical applications, combustible gas detection, $H_2S$ monitoring and hazardous leak detection.

In certain aspects of the present invention, a polymer-based sensor is used which exhibits a characteristic displayed by the human olfactory system in that it discriminates against ambient background gases in air such as $O_2$, $N_2$, and $CO_2$, and is more sensitive, based on the partial pressure of odorant in the gas phase, to odorants having lower vapor pressures. Thus, high odor detection thresholds are observed for odorants that have high vapor pressures and odorants with low vapor pressures generally have low odor detection thresholds.

It has been surprisingly discovered that the foregoing phenomenon can be explained using thermodynamic principles. For instance, at equilibrium, the chemical potential, $\mu$, of an odorant must be equal in both the sorbed and vapor phases (see, Schwarzenbach et al., *Environment Organic Chemistry*, (John Wiley & Sons, New York), pp. 681 (1993)). The equilibrium mole fraction, $\chi$, of the odorant in the sorbed phase is therefore related to the fraction of the vapor pressure of the odorant and to the chemical potential, by the relationships as set forth in Equations 1 and 2 below (see, Schwarzenbach et al., *Environment Organic Chemistry*, (John Wiley & Sons, New York), pp. 681 (1993)):

$$\mu = \mu^0 + RT \ln \gamma \chi \quad (1)$$

$$P/P^0 = a = \gamma \chi \quad (2)$$

In the foregoing equations, $\mu^0$ is the chemical potential of the odorant in its saturated vapor standard state, R is the universal gas constant, T is the temperature, $\gamma$ is the odorant activity coefficient, P is the partial pressure corresponding to 10% of the vapor pressure of the odorant, $P^0$ is the vapor pressure and a is the odorant activity.

In certain aspects, the activity coefficients, which account for the specific solvation interactions between the sorbent phase and the odorant molecules, are similar for odorants within a homologous series being sorbed into a given polymer. The concentration of any member of the homologous odorant series sorbed into a specific polymer will thus be primarily determined by the fraction of the vapor pressure of the odorant in the gas phase, as opposed to being determined primarily by the absolute concentration of the odorant in the vapor phase.

This situation is consistent with response trends of electronic nose sensors to homologous series of alkane and alcohol odorants. As set forth in Table 1 below, the variation in the activity coefficients, within two homologous series of odorants sorbing into the polymers used in an electronic nose, is small relative to the variation in the vapor pressures across the homologous series. These data indicate that the relative changes in the signals produced by the polymer composite sensors in response to exposures to members of each homologous series of odorants are, to first order, independent of specific binding features of the odorant into the polymer phase. Instead, the response intensities depend primarily on the equilibrium concentration of the odorant that is attained in the polymeric sensor material. Thus, dividing the events leading to the production of an electronic nose output signal into three components: 1) sorption of the odorant into the polymeric sensor material, 2) binding of the dissolved odorant molecule to specific signal transduction sites, and 3) molecularly-specific amplification events of the signals during the output stage, the data show that processes 2) and 3) are essentially constant for an electronic nose sensor response when compared to the human nose.

Figure 1B:
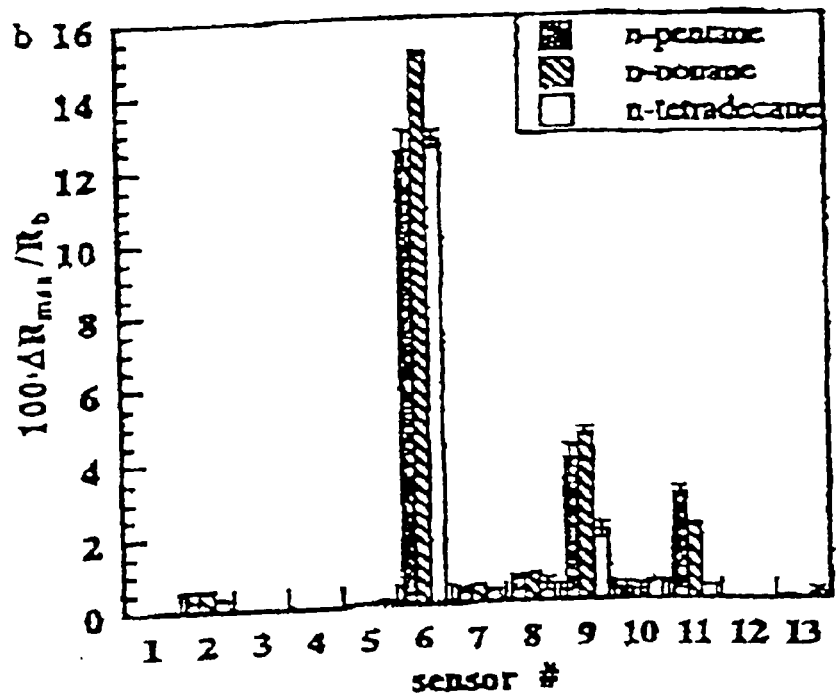

To illustrate this point, straight chain alcohols and straight chain alkanes were investigated as they define two homologous series of odorants that vary regularly in their chemical properties as the carbon chain length is increased (see, FIG. 1, Panel A and B, respectively). In addition, human psychophysical data on odor detection thresholds are available for these odorants (see, Devos, M. et al., *Standardized Human Olfactory Thresholds*, (Oxford University Press, New York), pp. 165 (1990)). This allows a comparison between electronic nose data and human olfaction data. With reference to FIG. 1, the responses $\Delta R_{max}/R_b$ are shown, wherein $R_b$ is the baseline resistance of the sensor immediately prior to the exposure to the analyte, and $R_{max}$ is the amplitude of the maximum resistance change during the 5 minutes the sensor was exposed to the analyte.

In this illustration, an array of carbon black-polymer composite sensors were exposed to methanol, 1-butanol, 1-octanol, n-pentane, n-nonane and n-tetradecane at partial pressure, P, corresponding to 10% of the vapor pressure of the odorant, $P^0$. The different response patterns across the array of sensors correspond to differences in odor quality data produced by the electronic nose, while the signal intensities correspond to differences in odor intensity that are obtained from the raw, unprocessed signals of the sensors.

TABLE 1

Activity coefficients for infinitely dilute straight chain alkanes and 1-alcohols in specific gas chromatography stationary phases.

| Odorant | Squalane | Tricresyl phosphate | Poly(vinyl acetate) | Poly-(ethylene oxide) | Poly-(ethylene glycol) |
| --- | --- | --- | --- | --- | --- |
| Ethane | 0.33 | | | | |
| Butane | 0.58 | 2.0 | | | 6.1 |
| Pentane | | | | 2.1 | |
| Hexane | 0.73 | 2.6 | 0.030 | 2.6 | 12 |
| Heptane | | | 0.040 | 3.3 | |
| Octane | 0.80 | 2.9 | 0.050 | 4.1 | 18 |
| Nonane | | | 0.082 | 5.2 | |
| Decane | 0.88 | 3.6 | 0.095 | 6.5 | 27 |
| Unedecane | | | 0.12 | 8.0 | |
| Dodecane | 0.93 | 4.3 | 0.15 | 8.8 | 42 |
| Tetradecane | | 5.1 | 0.23 | | 66 |
| Hexadecane | | 6.0 | 0.34 | | 83 |
| Octadecane | | 7.3 | | | 124 |
| Methanol | 5.4 | 1.0 | 0.0049 | | 0.63 |
| Ethanol | 4.1 | 1.3 | 0.0058 | 0.31 | 0.81 |

TABLE 1-continued

Activity coefficients for infinitely dilute straight chain alkanes and 1-alcohols in specific gas chromatography stationary phases.

| Odorant | Squalane | Tricresyl phosphate | Poly(vinyl acetate) | Poly-(ethylene oxide) | Poly-(ethylene glycol) |
|---|---|---|---|---|---|
| Propanol | 3.2 | 1.2 | 0.0081 | 0.29 | 0.93 |
| Butanol | 2.9 | 1.2 | 0.0093 | 0.41 | 1.1 |
| Pentanol | 2.5 | 1.2 | 0.011 | | 1.2 |
| Hexanol | 2.5 | 1.2 | 0.013 | | 1.5 |
| Heptanol | 2.5 | 1.3 | 0.015 | | 1.8 |
| Octanol | 2.6 | 1.2 | 0.018 | | 2.2 |
| Decanol | | | 0.026 | | |

Squalane, temperature = 373 K and molecular weight = 422.8 g/mol; tricresyl phosphate, temperature = 393 K and molecular weight = 368.4 g/mol; poly(vinyl acetate), temperature = 417 K and molecular weight ~ 500,000 g/mol; poly(ethylene oxide), temperature = 352 K and molecular weight ~ 1,000 g/mol; poly(ethylene glycol), temperature = 373 K and molecular weight = 300 g/mol.

Figure 2A:
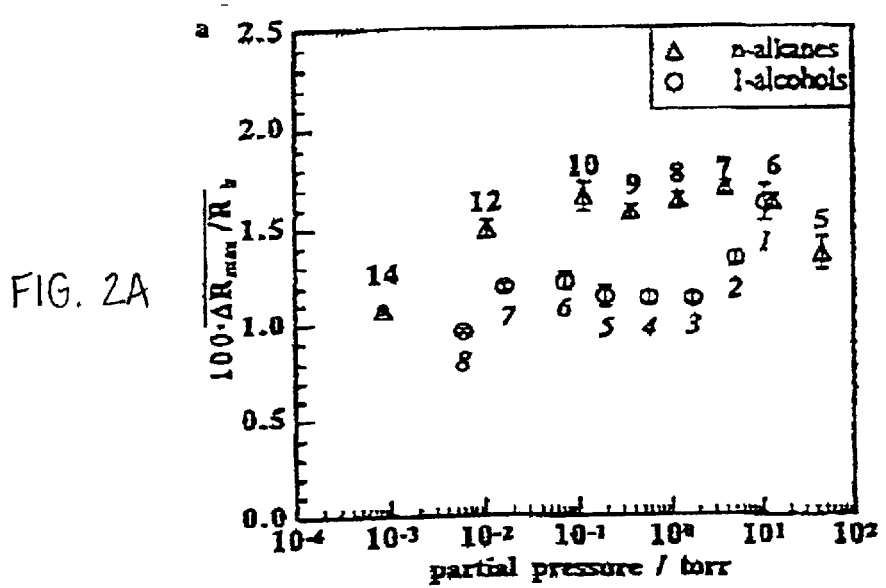
FIG. 2 Panel A–C shows various response intensities from 13 sensors in FIG. 1. Panel A shows the mean response intensity (signal response), $\Delta R_{max}/R_b$, defined as the average over all thirteen sensor responses in the electronic nose array to an odorant, plotted versus the partial pressures of homologous series of alkane and alcohol odorants. Panel B shows the responses, $\Delta R_{max}/R_b$, of three individual electronic nose sensors (poly(ethylene-co-vinyl acetate), poly(butadiene) and poly(n-butyl methacrylate), which produced the largest responses to a homologous series of straight chain alkanes, plotted versus the partial pressures of the odorants in each series. Panel C shows responses of three individual sensors (poly(ethylene glycol), poly(ethylene oxide) and poly(vinyl acetate)) that produced the largest responses to a straight chain homologous series of 1-alcohols, plotted versus the partial pressures of the odorants in each series. The alkanes used in Panel A and Panel B were: n-pentane, n-hexane, n-heptane, n-octane, n-nonane, n-decane, n-dodecane and n-tetradecane. The straight chain alcohols used in Panel A and Panel B were: methanol, ethanol, 1-propanol, 1-butanol, 1-pentanol, 1-hexanol, 1-heptanol and 1-octanol. Each odorant was maintained at a partial pressure equivalent to 10% of its vapor pressure, and the background was ambient air. For clarity, number of carbons in each odorant is indicated for each data point in italics for the alcohols and plain text for the alkanes. The error bars represent one standard deviation unit in the responses to 6 exposures of each odorant.
Figure 2B:
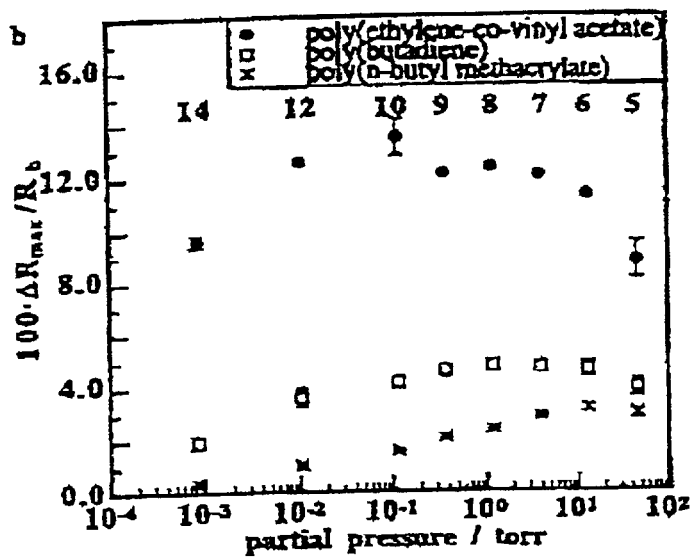
Figure 2C:
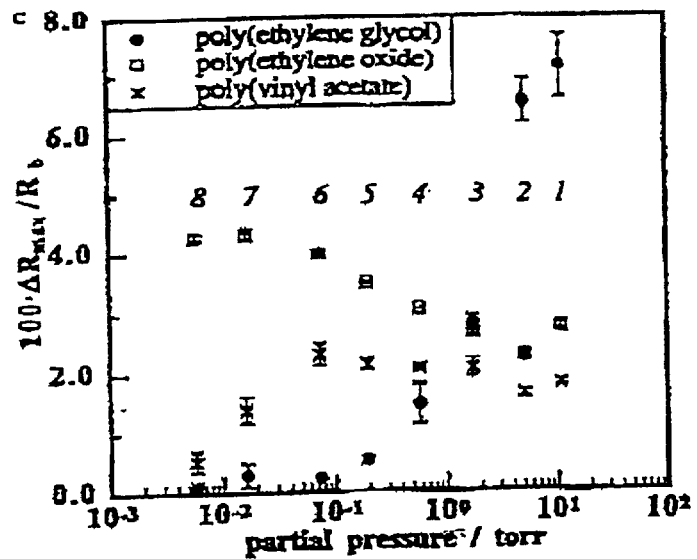

With reference to FIG. 2, Panel A, when the mean signal intensity, defined as the mean value of $\Delta R_{max}/R_b$ that was observed for all 13 sensors in the array upon exposure to an odorant, is plotted vs. the partial pressure of odorant present in the vapor phase, an electronic nose exhibits increased sensitivity, i.e., a similar response intensity to a lesser odorant concentration to lower vapor pressure alkanes and alcohols. In certain embodiments, the 13 polymers in the array of sensors were chosen to include a broad range of chemical properties, thereby minimizing biases that would result from averaging the responses over sets of sensors that had a limited chemical diversity.

An analogy to detection of an odorant at the human odor detection threshold, at which the presence of an odor can be identified as compared to a moist air blank, but the quality of the odor cannot be determined, can be obtained by plotting the trends in response intensity for the most strongly-driven sensors in the electronic nose towards the series of odorants studied. These data are displayed in FIG. 2, Panel B and Panel C for the alkanes and alcohols, respectively. These data confirm the trend observed in FIG. 2, Panel A, and show that the response intensity of an individual sensor is essentially independent of the odorant in the series, if the odorant is present in the gas phase at a constant fraction of its vapor pressure.

As such, in another embodiment, the present invention relates to a method for validating that a sensor array response intensity matches a human nose detection threshold, the method comprising:
  (a) contacting the sensor array with a constant fraction of a known vapor pressure of a first odorant to produce a first response intensity;
  (b) contacting the sensor array with the constant fraction of a known vapor pressure of a second odorant to produce a second response intensity; and
  (c) comparing the first response intensity to the second response intensity, thereby validating that the sensor array response intensity matches the human nose detection threshold.

In an illustrative example of the foregoing validation method, a first odorant is pentane and a second odorant is tetradecane. The vapor pressure of pentane is 46 torr in 707 torr of air. The vapor pressure of tetradecane is $8.5 \times 10^{-4}$ torr in 707 torr of air. Thus, the electronic nose produced nearly the same odor intensity from their raw signal outputs for $P=0.1 \cdot P^0$ of pentane ($P=46$ torr in 707 torr of air 61 part per thousand) as they did for $P=0.1 \cdot P^0$ of tetradecane ($P=8.5 \cdot 10^{-4}$ torr in 707 torr air=1.1 parts per million). In this example, the sensor array intensity is validly matching the intensity response of that of a human nose because 10% of the vapor pressure of the first odorant has the same response intensity as 10% of the vapor pressure of the second odorant.

Figure 3:
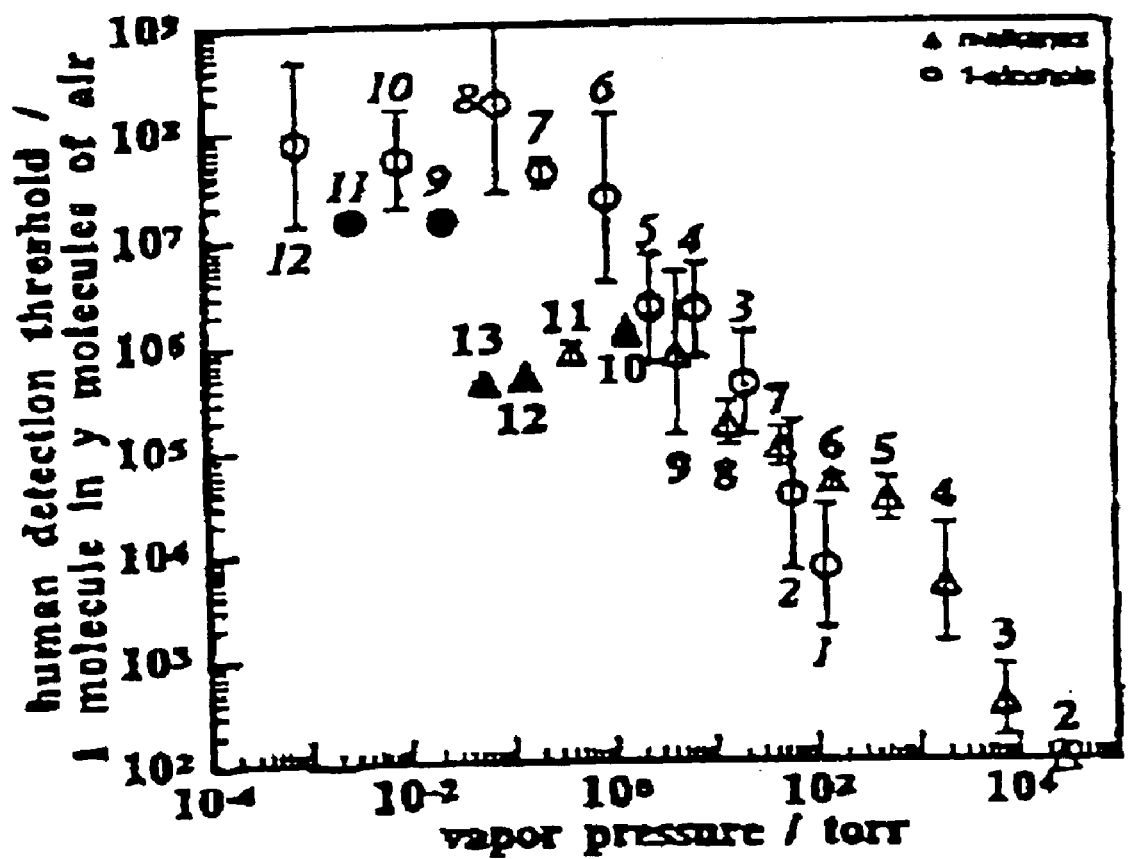
FIG. 3 shows a plot of human olfactory detection thresholds versus the vapor pressure (at 25° C.) of a homologous series of straight chain alkanes, ranging from ethane to tridecane, and of 1-alcohols ranging from methanol to dodecanol. For clarity, the number of carbons in each odorant is indicated next to the corresponding data point, in italics for the alcohols and plain text for the alkanes. An average human can detect one odorant molecule in the number of air molecules plotted on the ordinate. The error bars represent one standard deviation unit in the standardized results reported by at least two, and up to twenty, authors (Devos, M. et al., *Standardized Human Olfactory Thresholds*, (Oxford University Press, New York), pp. 165 (1990)). A filled data point is used if only one author reported results. A best straight line fit through the alcohols from methanol to octanol gives a slope of $-1.3\pm0.1$ and an $r^2$ value of 0.96. Similarly, a best straight line fit through the alkanes from ethane through decane gives a slope of $-0.94\pm0.08$ and an $r^2$ value of 0.96.

With reference to FIG. 3, human odor detection thresholds are set forth as mean values. These detection threshold values were compiled from several published sets of psychophysical data, for the 1-alcohol and n-alkane homologous series of odorants (see, Devos et al., *Standardized Human Olfactory Thresholds*, (Oxford University Press, New York), pp. 165 (1990)). Analogously to the electronic nose signals, these mean human olfactory odor detection thresholds, when based on odorant partial pressure, increase as the vapor pressure of the odorant increases. When the data are referenced to the fraction of the room temperature vapor pressure of each odorant, the mean literature detection thresholds are essentially constant across this vapor pressure range for the various odorants in the series. At vapor pressures below approximately 1 torr, the thresholds appear to plateau.

The mean human olfactory detection thresholds for a series of odorants match that of the electronic nose. The human data are thus consistent with the olfactory detection thresholds for these odorants and are dictated primarily by a physical sorption effect. Thus, the comparison between the human and electronic nose response data is consistent with a common sorption-based effect dominating the odor intensity trends. Deviations from this behavior indicates variations in chemical interactions between odorants and the olfactory receptors, for example, the trend of decreasing odor intensity thresholds for odorants with lower vapor pressures is not observed for alkylamines or alkylthiols (see, Devos, M. et al., *Standardized Human Olfactory Thresholds*, (Oxford University Press, New York), pp. 165 (1990)).

Figure 5A:
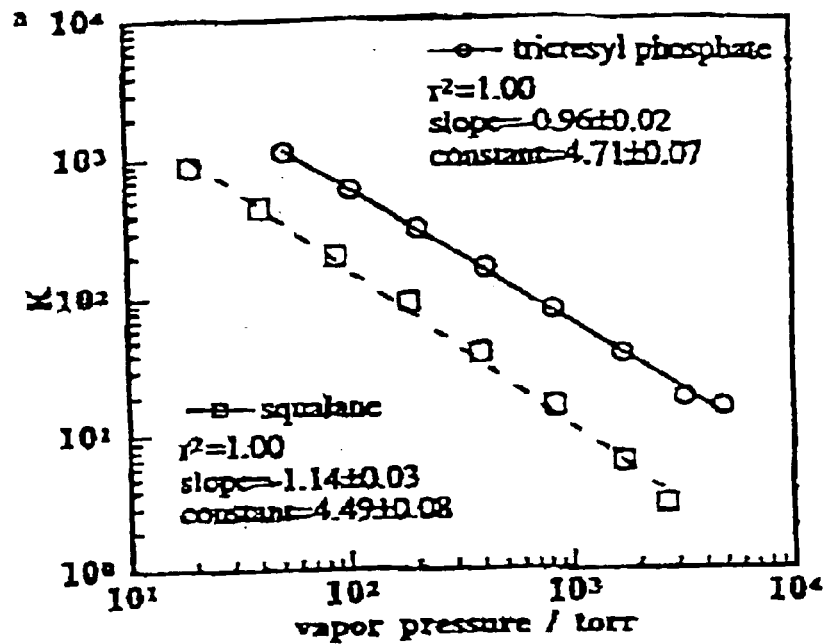
FIGS. 5A-B shows a plots of the partition coefficient, K, versus the vapor pressure of homologous series. Panel A illustrates the 1-alcohols. Panel B illustrates the n-alkanes on the squalane stationary phase at 100° C. and the tricresyl phosphate stationary phase at 120° C. The series of alcohols plotted in Panel A ranged from methanol to 1-octanol inclusively. The series of alkanes plotted in Panel B consisted of even carbon n-alkanes ranging from ethane to n-dodecane inclusively on the squalane stationary phase and n-butane to n-octadecane inclusively on the tricresyl phosphate stationary phase. The lines indicate the best linear fits and the fitting parameters are given in the figures.
Figure 5B:
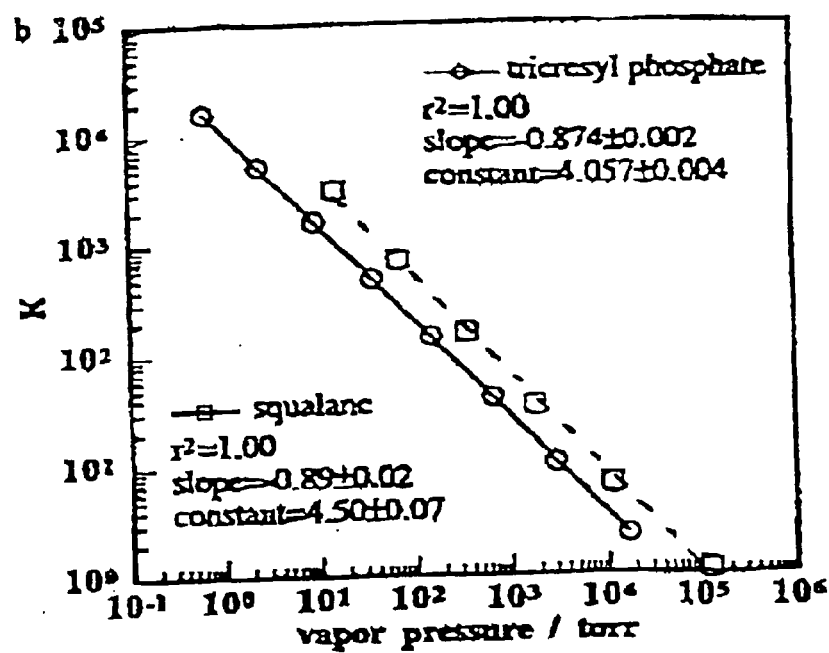

At a given odorant activity in a sorption layer, such as a polymeric film or in the epithelium for the human olfactory system, there is some variation in sorbed odorant concentration, and in the resulting signal response, for different polymer (receptor) types. Otherwise it would be impossible to obtain odor quality information from the output of an array of sensing elements. In the electronic nose, differential sorption of odorants, with varying activity coefficients, into the various polymers produces a differential swelling, and therefore produces the differential output pattern of signals that can be used to identify odorants (see, FIG. 1, Panel A and B). Similarly, from the gas chromatographic partition coefficient data of FIG. 5, Panel A and B, it is clear that the alcohols sorb preferentially into the polar support (tricresyl phosphate) over the nonpolar support (squalane), while the alkanes exhibit the opposite trend and sorb preferentially into the nonpolar support relative to the polar support.

These differences in signal intensity are clearly due to specific chemical interactions between the odorant and polymer molecules, as reflected in the variation in activity coefficients, that act in conjunction with the sorption effects expected for an ideal sorbent solute system to determine the response of an individual detector in the array to the odorant of concern. For odorants, the response intensity of the electronic nose sensors is determined, to first order, by the thermodynamic activity effects that dictate the concentration of odorant into the film. The smaller deviations from the mean response intensity exhibited by the various individual sensors produce the outputs that can be used to extract odor quality information from the array.

Figure 4A:
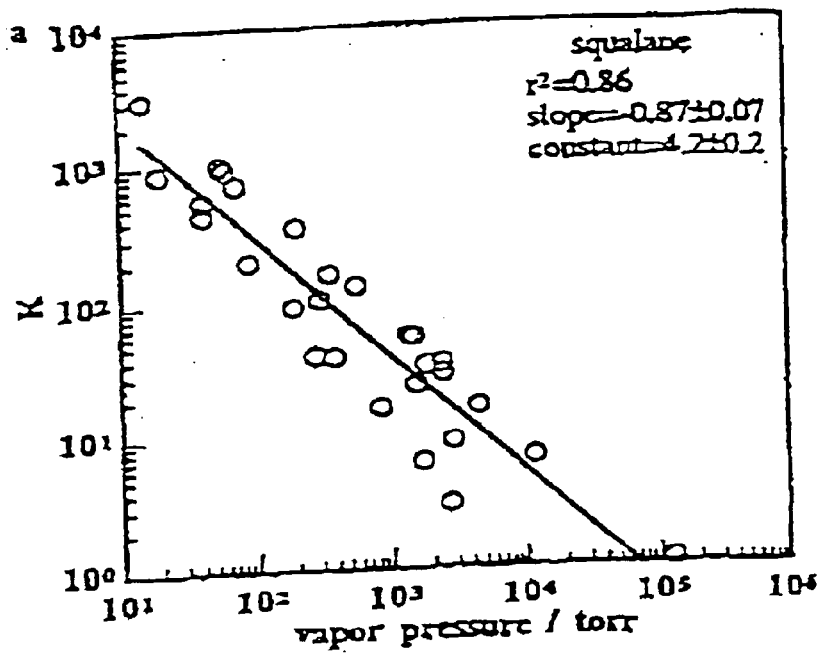
FIGS. 4A-B shows plots of partition coefficients. Panel A plots of the partition coefficients, K, for odorant's sorbing into the stationary phases of squalane at 100° C. Panel B plots tricresyl phosphate at 120° C. obtained from gas chromatography data (McReynolds, W. O., *Gas Chromatographic Retention Data*, (Preston Technical Abstracts Co., Evanston, Ill.), pp. 335 (1966)), versus odorant vapor pressure. The odorants plotted in both plots are: methanol, ethanol, acetone, dichloromethane, 1-propanol, ethyl acetate, 2,3-dimethyl n-butane, n-hexane, chloroform, 1-butanol, 2-chloroethanol, tetrachloromethane, benzene, 1-pentanol, cyclopentanone, toluene, n-octane, 1-hexanol, 1-heptanol, 2-octanol, n-decane, n-butane, 1-butane and n-dodecane. Additional odorants plotted only in Panel A are: ethane, m-diethylbenzene, o-diethylbenzene and o-xylene. Additional odorants plotted only in Panel B are: ethylene glycol diacetate, n-hexadecane, n-tetradecane and n-octadecane. The solid lines represent the best line fits through the data points, with the fitting parameters given in the figures;.
Figure 4B:
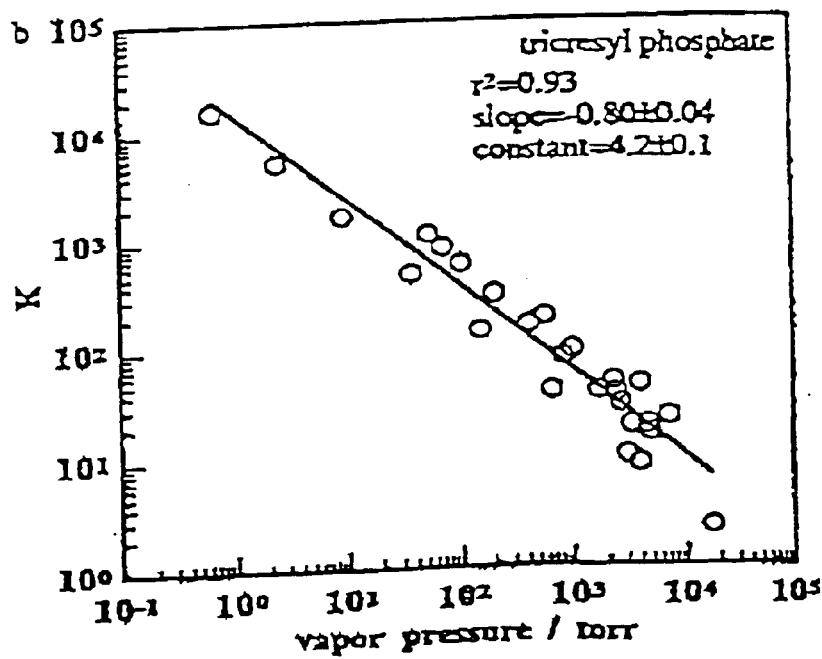

With reference to FIGS. 2 and 3, retention volumes for odorants having a wide range of vapor pressures were converted into gas/support partition coefficients (see, Littlewood, A. B., *Gas Chromatography*, (Academic Press, New York), pp. 514 (1962)), K, and the data were collated for two selected stationary phases, one polar (tricresyl phosphate) and one nonpolar (squalane) in character. The values of log K for each odorant into each sorbent phase were then regressed against log P⁰ for every odorant in the data set. With reference to FIG. 4, Panels A–B, the regressions yielded straight lines with slopes of −0.87±0.07 and −0.80±0.04 and $r^2$ values of 0.86 and 0.93 respectively. Slopes were approximately −1.0 and $r^2$ values were 1.0 for both the alcohol and alkane homologous series (see, FIG. 5, Panels A–B). This reduction in variance is expected because the variation in chemically based gas/support partition coefficients that contribute to the variance in the entire data set is reduced when only partition coefficients for a series of homologous odorants are considered. The activity coefficients at infinite dilution for these series of alcohols and alkanes in the two stationary phases are set forth in Table 1 (McReynolds, W. O., *Gas Chromatographic Retention Data*, (Preston Technical Abstracts Co., Evanston, Ill.), pp. 335 (1966)). It is apparent that the activity coefficients for members of each homologous series are relatively similar to the variation in vapor pressures, which spans many orders of magnitude, for each series of odorants.

In certain aspects, activity coefficient data were also obtained from the literature (McReynolds, W. O., *Gas Chromatographic Retention Data*, (Preston Technical Abstracts Co., Evanston, Ill.), pp. 335 (1966); Hao, W. et al., *Polymer Solution Data Collection*, (DECHEMA, Frankfurt), pp. 365 (1992)) for some of the specific polymers in the electronic nose sensors. Data for poly(vinyl acetate), poly(ethylene oxide) and poly(ethylene glycol) are set forth in Table 1. The activity coefficients at infinite dilution for the odorants within either the alcohol or alkane series, sorbed into these specific polymers, are clearly similar relative to the large variation in their vapor pressures.

All publications, patents and patent applications mentioned in this specification are herein incorporated by reference into the specification in their entirety for all purposes. Although the invention has been described with reference to preferred embodiments and examples thereof, the scope of the present invention is not limited only to those described embodiments. As will be apparent to persons skilled in the art, modifications and adaptations to the above-described invention can be made without A departing from the spirit and scope of the invention, which is defined and circumscribed by the appended claims.

What is claimed is:

1. A method for validating that a sensor array detection ability mimics a human nose detection ability, the method comprising:
   (a) contacting said sensor array with a constant fraction of a known vapor pressure of a first odorant to produce a first response intensity;
   (b) contacting said sensor array with a constant fraction of a known vapor pressure of a second odorant to produce a second response intensity;
   (c) comparing said first response intensity to said second response intensity; and
   (d) adjusting said first and second response intensities to match the mean human olfactory odor detection thresholds for said first and second odorants.

2. A method in accordance with claim 1, wherein said sensor array comprises at least two sorption-based sensors which are members selected from the group consisting of a chemiresistors, a conducting/nonconducting regions sensor, a SAW sensor, a metal oxide gas sensor, a bulk conducting polymer sensor, a Langmuir-Blodgett film sensor, and combinations thereof.

3. A method in accordance with claim 2, wherein said sensor is a conducting/nonconducting regions sensor.

4. A method in accordance with claim 2, wherein said sensor is a bulk conducting polymer sensor.

5. A method in accordance with claim 3, wherein said nonconducting region is an organic polymer.

6. A method in accordance with claim 5, therein said organic polymer is a member selected from the group consisting of (poly(4-vinyl phenol), poly(α-methyl styrene), poly(vinyl acetate), poly(sulfone), poly(caprolactone), poly (ethylene-co-vinyl acetate), poly(ethylene oxide), poly (ethylene), poly(butadiene), poly(vinylidine fluoride), poly (n-butyl methacrylate), poly(epichlorohydrin) and poly (ethylene glycol)).

7. A method in accordance with claim 1, wherein said odorant is a member selected from the group consisting of alkanes, alkenes, alkynes, dienes, alicyclic hydrocarbons, arenas, alcohols, ethers, ketones, aldehydes, carbonyls, carbanions, heterocycles, polynuclear aromatics, organic derivatives, biomolecules, microorganisms, bacteria, viruses, sugars, nucleic acids, isoprenes, isoprenoids, fatty acids and their derivatives.

8. A method for validating that a sensor array detection ability mimics a human nose detection ability, the method comprising:
   (a) contacting said sensor array with a first odorant with a first vapor pressure to produce a first response intensity;
   (b) contacting said sensor array with a second odorant with a vapor pressure lower than said first vapor pressure to produce a second response intensity;
   (c) determining a difference between a mean human olfactory detection threshold for the first odorant and mean human olfactory detection threshold for the second odorant; (d) comparing said first response intensity to said second response intensity; and (e) adjusting said first and second response intensities so that said second response intensity is lower than said first response intensity so that a comparison between said first and second response intensities directly correlates to the difference between the mean human olfactory thresholds for the first and second odorants, thereby matching the sensor array detection ability to a human nose detection ability.

9. The method of claim 1, wherein said constant fraction is 10%.

10. A method for validating that a sensor array detection ability mimics a human nose detection ability, the method comprising:
    (a) contacting said sensor array with a 10% fraction of a known vapor pressure of a first odorant to produce a first response intensity;
    (b) contacting said sensor array with a 10% fraction of a known vapor pressure of a second odorant to produce a second response intensity;
    (c) comparing said first response intensity to said second response intensity; and
    (d) adjusting said first and second response intensities to be substantially identical.

11. A method in accordance with claim 10, wherein said sensor array comprises at least two sorption-based sensors which are members selected from the group consisting of a chemiresistors, a conducting/nonconducting regions sensor, a SAW sensor, a metal oxide gas sensor, a bulk conducting polymer sensor, a Langmuir-Blodgett film sensor, and combinations thereof.

* * * * *